United States Patent
Yellin

(10) Patent No.: US 9,706,937 B2
(45) Date of Patent: Jul. 18, 2017

(54) VENTRICULAR ELECTRICAL ACTIVITY INDICATOR

(71) Applicant: BIOSENSE WEBSTER (ISRAEL) LTD., Yokneam (IL)

(72) Inventor: Tamir Avraham Yellin, Yokneam Hamoshava (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 160 days.

(21) Appl. No.: 14/693,042

(22) Filed: Apr. 22, 2015

(65) Prior Publication Data
US 2016/0310030 A1    Oct. 27, 2016

(51) Int. Cl.
| | | |
|---|---|---|
| A61B 5/0452 | (2006.01) | |
| A61B 5/00 | (2006.01) | |
| A61B 5/042 | (2006.01) | |
| A61B 5/044 | (2006.01) | |
| A61B 18/14 | (2006.01) | |
| A61B 18/00 | (2006.01) | |

(52) U.S. Cl.
CPC ............ *A61B 5/0452* (2013.01); *A61B 5/044* (2013.01); *A61B 5/0422* (2013.01); *A61B 5/743* (2013.01); *A61B 5/6852* (2013.01); *A61B 5/6859* (2013.01); *A61B 18/1492* (2013.01); *A61B 2018/00577* (2013.01); *A61B 2018/00839* (2013.01)

(58) Field of Classification Search
CPC ....... A61B 5/0452; A61B 5/743; A61B 5/044; A61B 5/0422; A61B 5/6852; A61B 5/6859; A61B 18/1492; A61B 2018/00839; A61B 2018/00577
See application file for complete search history.

(56) References Cited

U.S. PATENT DOCUMENTS

| | | |
|---|---|---|
| 6,226,542 B1 | 5/2001 | Reisfeld |
| 6,301,496 B1 | 10/2001 | Reisfeld |
| 6,814,733 B2 | 11/2004 | Schwartz et al. |
| 6,892,091 B1 | 5/2005 | Ben-Haim et al. |
| 6,997,924 B2 | 2/2006 | Schwartz et al. |
| 7,156,816 B2 | 1/2007 | Schwartz et al. |
| 7,536,218 B2 | 5/2009 | Govari et al. |
| 7,756,576 B2 | 7/2010 | Levin |
| 2013/0274582 A1 | 10/2013 | Afonso et al. |
| 2014/0005664 A1 | 1/2014 | Govari et al. |
| 2014/0058246 A1 | 2/2014 | Boveja et al. |

FOREIGN PATENT DOCUMENTS

EP        2689722 A1      1/2014

OTHER PUBLICATIONS

EP 16 16 6410 Search Report dated Sep. 30, 2016.

*Primary Examiner* — Mark W Bockelman
(74) *Attorney, Agent, or Firm* — Notaro, Michalos & Zaccaria P.C.

(57) ABSTRACT

Cardiac catheterization is carried out using a probe having sensing electrodes disposed on a distal portion thereof, placing the sensing electrodes in galvanic contact with respective locations in an atrium of the heart, thereafter acquiring electrograms from the sensing electrodes while concurrently detecting ventricular depolarization events, generating from the electrograms a time-varying electroanatomic map showing electrical propagation in the heart, and displaying the electroanatomic map in a series of visual images, the images including an icon that visually indicates the ventricular depolarization events.

20 Claims, 6 Drawing Sheets

VENTRICULAR ELECTRICAL ACTIVITY INDICATOR

BACKGROUND OF THE INVENTION

Field of the Invention

This invention relates to medical imaging systems. More particularly, this invention relates to operator interfaces in medical imaging systems.

Description of the Related Art

Cardiac arrhythmias, such as atrial fibrillation, occur when regions of cardiac tissue abnormally conduct electric signals to adjacent tissue, thereby disrupting the normal cardiac cycle and causing asynchronous rhythm.

Electrical activity in the heart is typically measured by advancing a multiple-electrode catheter to measure electrical activity at multiple points in the heart chamber simultaneously. A graphical user interface integrated with modern imaging systems for monitoring cardiac catheterization presents an abundance of dynamically changing information from the multiple electrodes to the operator, and facilitates efficient processing of the information by the operator.

Receiving atrial electrogram signals from intracardiac catheters is complicated by undesirable far field signal component mixed with near field electrical signals. In this environment near field signals indicate local activation, i.e., propagation of a signal through local regions being sensed by the electrodes. Detection of local activation is widely employed as an electrophysiological indicator of the local state of the heart. The far field electrical signals contain no useful information about local heart activation and only disturb the measurements.

Commonly assigned U.S. Patent Application Publication No. 2014/0005664 by Govari et al., which is herein incorporated by reference, discloses distinguishing a local component in an intracardiac electrode signal, due to the tissue with which the electrode is in contact from a remote-field contribution to the signal, and explains that a therapeutic procedure applied to the tissue can be controlled responsively to the distinguished local component.

SUMMARY OF THE INVENTION

Modern imaging systems adapted to cardiac electrophysiology produce dynamic functional electroanatomic maps of the heart, such as a time-varying map of local activation times (LAT), also known as a 4-dimensional LAT map. However, an operator who is attempting to annotate atrial activation onset times using a multi-electrode catheter and is presented with conventional maps of this sort may experience difficulty distinguishing near-field atrial activity from far-field ventricular activity.

According to disclosed embodiments of the invention, an indication of ventricular depolarization is visualized on a 4-dimensional LAT map as an icon, which is presented using the same time-window and color scale as the dynamic map, but is time-referenced to ventricular activity, e.g., an R-wave or QRS complex rather than to a local activation time of a point or region of the heart.

There is provided according to embodiments of the invention a method for guiding a medical procedure, which is carried out by inserting into a heart of a living subject a probe having sensing electrodes disposed on a distal portion thereof, placing the sensing electrodes in galvanic contact with respective locations in an atrium of the heart, thereafter acquiring electrograms from the sensing electrodes while concurrently detecting ventricular depolarization events, generating from the electrograms a time-varying electroanatomic map showing electrical propagation in the heart, and displaying the electroanatomic map in a series of visual images, the images including an icon that visually indicates the ventricular depolarization events.

The icon may be spaced apart from the electroanatomic map on the images. Alternatively, the icon may be positioned on the electroanatomic map at a center of mass of a ventricle of the heart.

An aspect of the method includes indicating local activation times for the respective locations on the electroanatomic map.

A further aspect of the method includes detecting on the electroanatomic map an indication of atrial depolarization in at least one of the respective locations, making a determination from a visual state of the icon that an instance of ventricular depolarization has occurred concurrently with the indication of atrial depolarization, and reporting responsively to the determination that the indication of atrial depolarization is a suspect false annotation event.

There is further provided according to embodiments of the invention an apparatus, including a processor connectable to an electrocardiographic sensor of ventricular activity and to a cardiac catheter having at least one sensing electrode disposed on a distal portion thereof. The apparatus includes a display linked to the processor, a memory accessible to the processor having programs and data objects stored therein. The programs include a graphical interface program. When the at least one sensing electrode is in galvanic contact with respective locations in an atrium of a heart, execution of the programs cause the processor to acquire electrograms from the at least one sensing electrode and concurrently detect ventricular depolarization events in the heart via the electrocardiographic sensor. The processor is further caused to generate from the electrograms a time-varying electroanatomic map showing electrical propagation in the heart, and to invoke the graphical interface program to present the electroanatomic map on the display as a series of visual images. The images include an icon that visually indicates the ventricular depolarization events.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as a USB memory, hard drive, electronic media or CD-ROM. The code may be distributed on such media, or may be distributed to users from the memory or storage of one computer system over a network of some type to storage devices on other computer systems for use by users of such other systems.

DEFINITIONS

"Annotations" refer to points on an electrogram that are considered to denote events of interest. In this disclosure the events are typically onset of the propagation of an electrical wave (local activation time) as sensed by an electrode.

Overview

Figure 1:
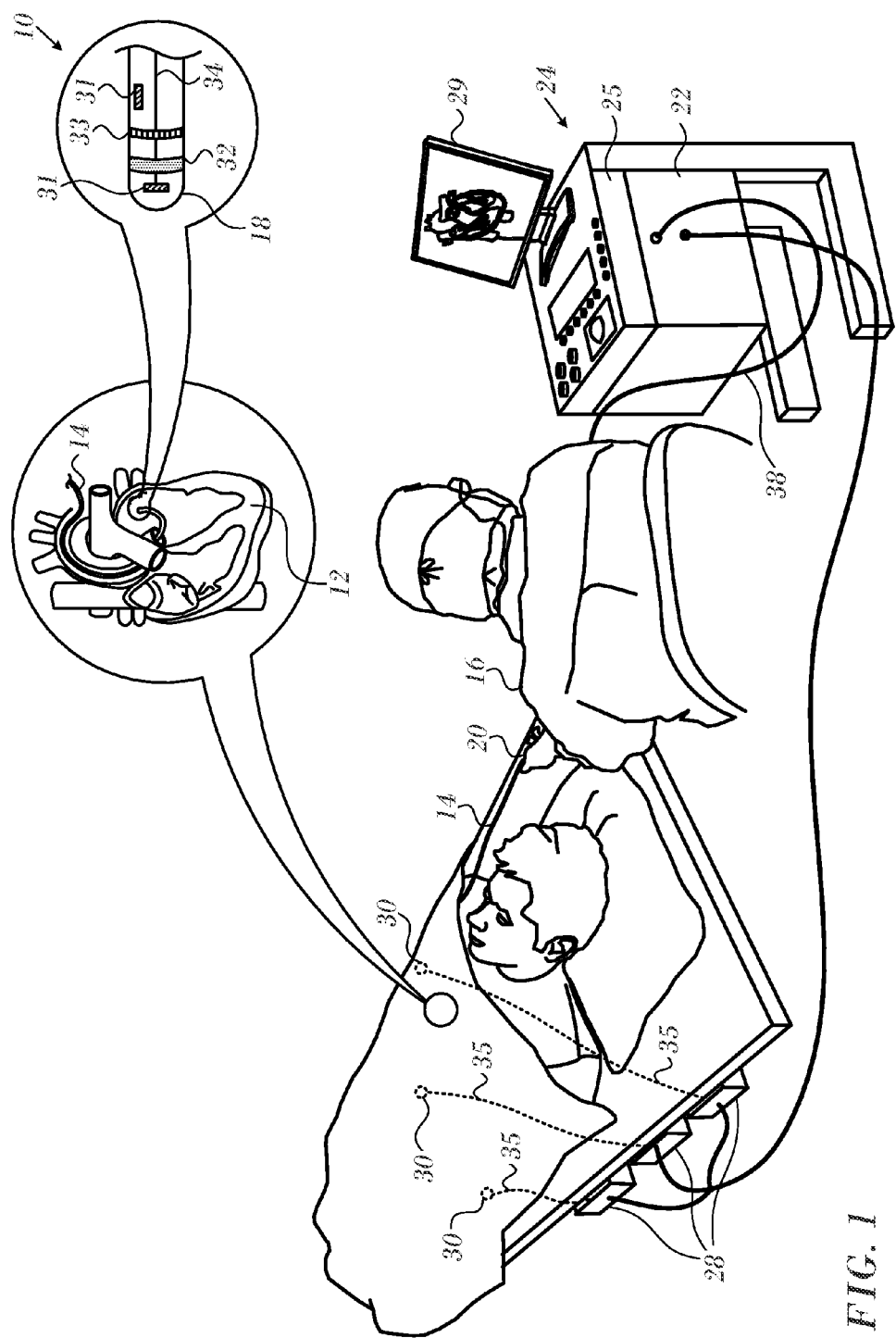
FIG. 1 is a pictorial illustration of a system for performing medical procedures in accordance with an embodiment of the invention.

Turning now to the drawings, reference is initially made to FIG. 1, which is a pictorial illustration of a system 10 for performing diagnostic and therapeutic procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at an ablation target site. Functional electroanatomic maps, e.g., electrical activation maps may then be prepared, according to the methods disclosed in U.S. Pat. Nos. 6,226, 542, and 6,301,496, and in commonly assigned U.S. Pat. No. 6,892,091, whose disclosures are herein incorporated by reference. One commercial product embodying elements of the system 10 is the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 60° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a position processor 22, located in a console 24.

Ablation energy and electrical signals can be conveyed to and from the heart 12 through one or more electrodes 32 located at or near the distal tip 18 via cable 34 to the console 24. Pacing signals and other control signals may be conveyed from the console 24 through the cable 34 and the electrodes 32 to the heart 12. One or more sensing electrodes 33, also connected to the console 24, are disposed near the ablation electrode 32 and have connections to the cable 34.

Wire connections 35 link the console 24 with body surface electrodes 30 and other components of a positioning sub-system. The electrodes 32 and the body surface electrodes 30 may be used to measure tissue impedance at the ablation site as taught in U.S. Pat. No. 7,536,218, issued to Govari et al., which is herein incorporated by reference. A temperature sensor such as thermocouples 31, may be mounted on or near the ablation electrode 32 and optionally or near the sensing electrodes 33.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

The positioning processor 22 is an element of a positioning subsystem in the system 10 that measures, inter alia, location and orientation coordinates of the catheter 14.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem may employ impedance measurement, as taught, for example in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to execute a graphical user interface program that is operative to produce the visual displays described below by driving a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14, and to analyze the electrical signals from the electrodes.

Typically, the system 10 includes other elements, which are not shown in the figures for the sake of simplicity. For example, the system 10 may include an electrocardiogram (ECG) monitor, coupled to receive signals from one or more body surface electrodes, to provide an ECG synchronization signal and signal ventricular depolarization events to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided.

With modern imaging systems used for monitoring cardiac catheterization, an increasing abundance of dynamically changing information is presented to the operator, to the extent that efficient processing of the information by the operator is impaired. Modern navigation and ablation catheters typically have multiple sensors, sensing electrodes, and ablation electrodes, which can be active in many combinations. Each of these has its own time-varying status, which is important for the operator to evaluate concurrently with extensive electroanatomic information regarding cardiac function.

User Interface

Figure 2:
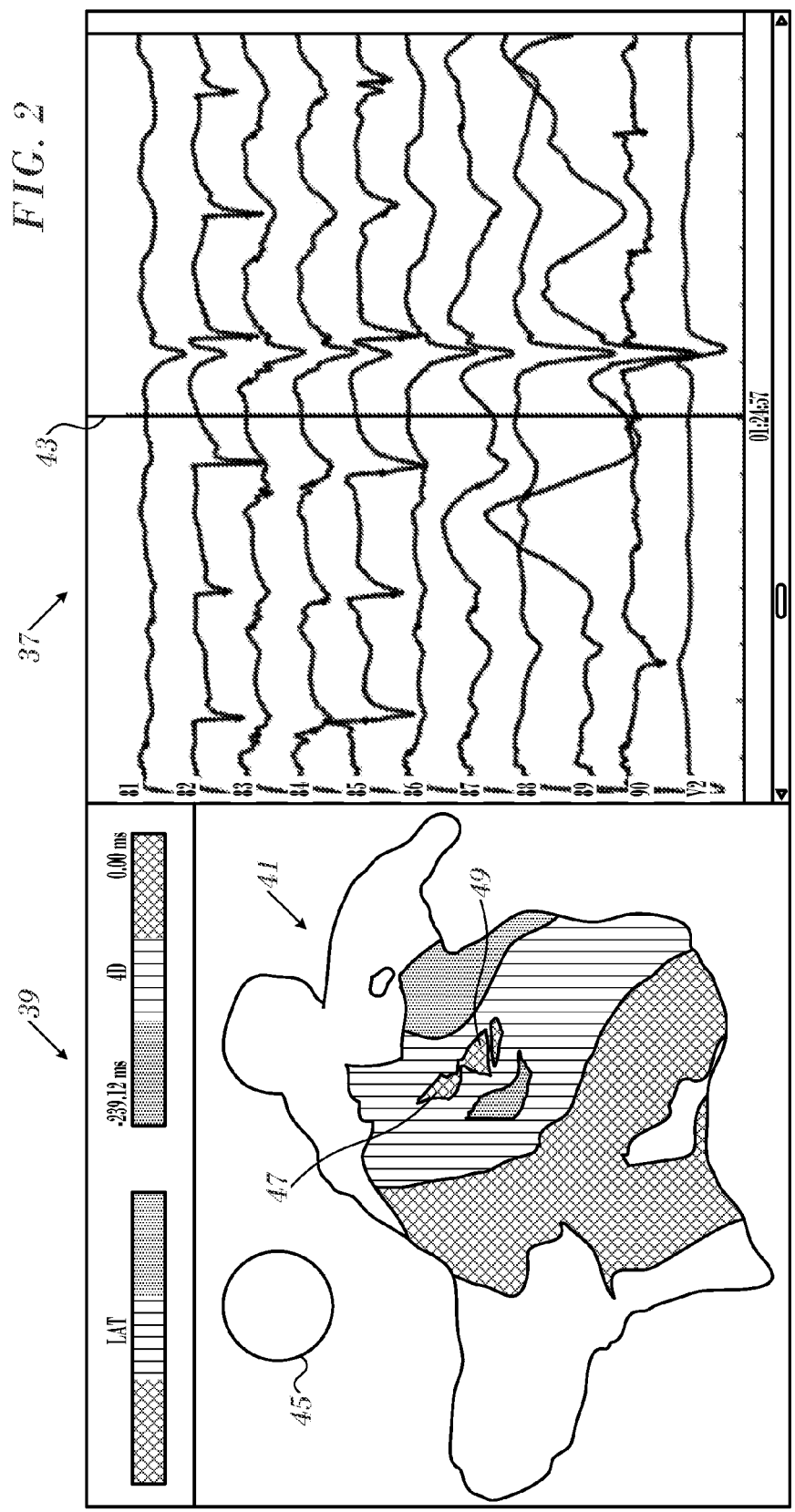
FIG. 2 is a screen display generated by the system shown in FIG. 1 in accordance with an embodiment of the invention.

Reference is now made to FIG. 2, which is a typical screen display of an electroanatomic map of the left atrium, which is generated by the graphical user interface program on monitor 29 by the system 10 (FIG. 1), in accordance with an embodiment of the invention. Right pane 37 shows electrograms obtained from multiple electrodes catheter. Left pane 39 presents a snapshot of a 4-dimensional LAT map 41 that was obtained at a time corresponding to vertical line 43 in the right pane 37. A spherical icon 45 activates upon detection of an R-wave or QRS complex in one of the tracings or in another ECG lead (not shown). In the snapshot of the left pane 39, the icon 45 is not activated, suggesting that signals being received from atrial regions 47, 49 at the time of the snapshot are not far-field signals from the ventricle. While the icon 45 is spherical, both its shape and its location with respect to the map 41 are exemplary and not limiting. Other shapes and locations of the icon 45 are possible, so long as the relative states of activation of the icon and the atria are readily presented to the operator.

In one embodiment the icon 45 is spaced apart from the map 41. Alternatively, the icon 45 may be placed approximately the center of mass of the ventricles. In any case, visual indicia, e.g., coloring of the icon 45, are referenced to detections of ventricular depolarization, such as an R wave or QRS complex. The color scale for the icon 45 and the map 41 should be the same, in order to facilitate its interpretation by the operator. A different color scale would be less intuitive, and even confusing to the operator. It would likely create a distorted impression of the information displayed on the map.

Figure 3:
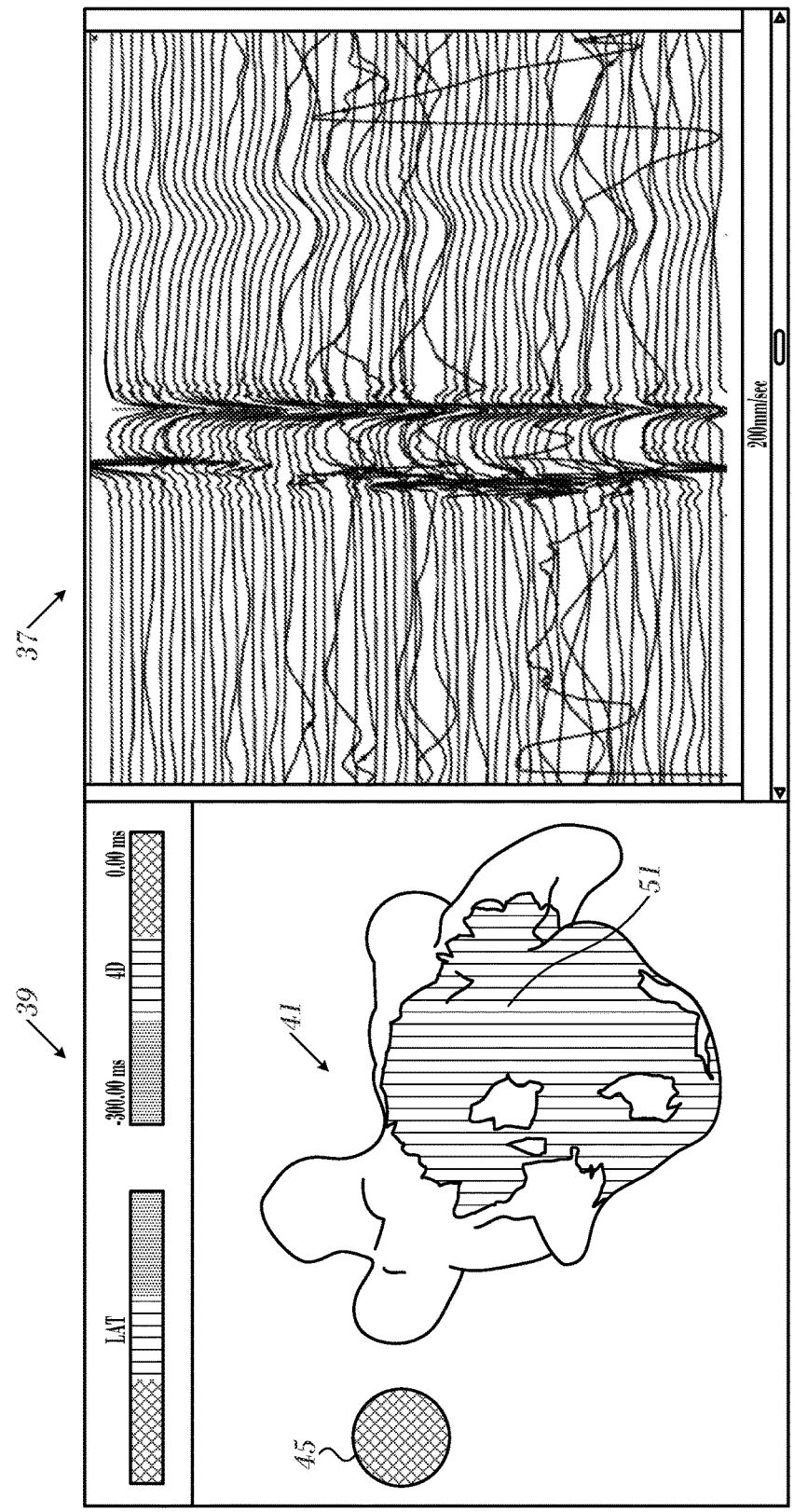
FIG. 3 is a screen display generated by the system shown in FIG. 1 in accordance with an embodiment of the invention.

Reference is now made to FIG. 3, which is a screen display similar to FIG. 2, in accordance with an embodiment of the invention. Atrial depolarization is detected in atrial region 51. The icon 45 is active, indicating that ventricular depolarization has occurred. However the activation time is not consistent with the activation times of the atrial region 51. It may be concluded with confidence that the signals received at the time of the snapshot from the atrial region 51 are not affected by far-field signals from the ventricle.

Figure 4:
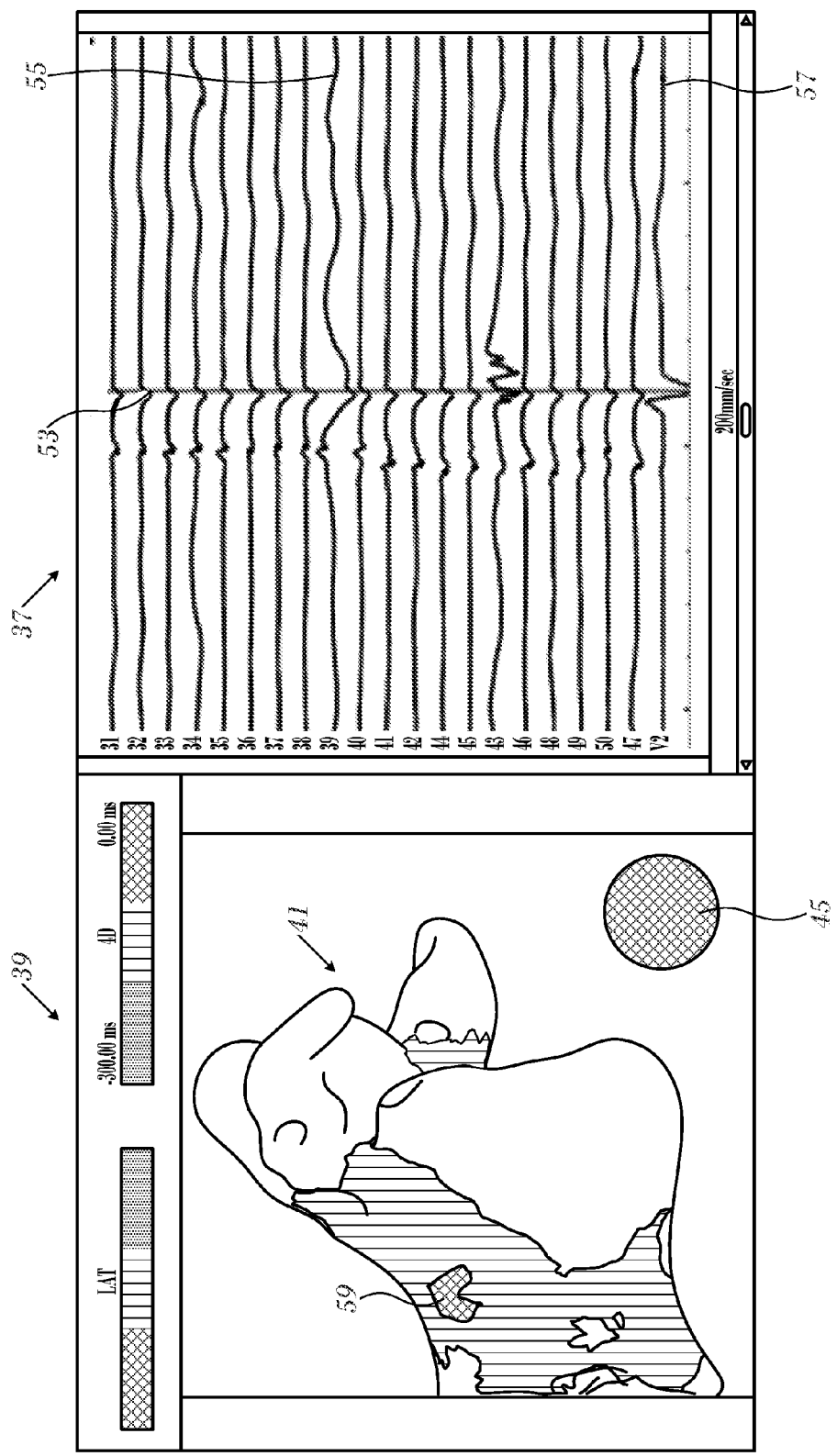
FIG. 4 is a screen display generated by the system shown in FIG. 1 in accordance with an embodiment of the invention.

Reference is now made to FIG. 4, which is another screen display similar to FIG. 2 showing the posterior wall of the atria, in accordance with an embodiment of the invention. The snapshot of the 4-dimensional LAT map is obtained at a time corresponding to vertical line 53. At this time activity is noted on tracing 55 and a concurrent deflection indicative of ventricular depolarization is seen on tracing 57. The icon 45 is active, consistent with the occurrence of ventricular depolarization. An atrial region 59 is monitored by a lead from which the tracing 55 was obtained. The region 59 shows apparent activation in the region of the sino-atrial (SA) node; however, because it is concurrent with the activation of the icon 45, the region 59 cannot be reliably interpreted on this snapshot, as the lead may have detected far-field ventricular activity While the operator could reference the tracing 57, evaluate the ordered atrial activations on the right pane, and deduce that the activation of region 59 as well as activations of neighboring regions are inconsistent with physiologic SA node activation, the illuminated state (or other visual appearance) of the icon 45 relieves the operator from the burden of this sort of analysis.

Figure 5:
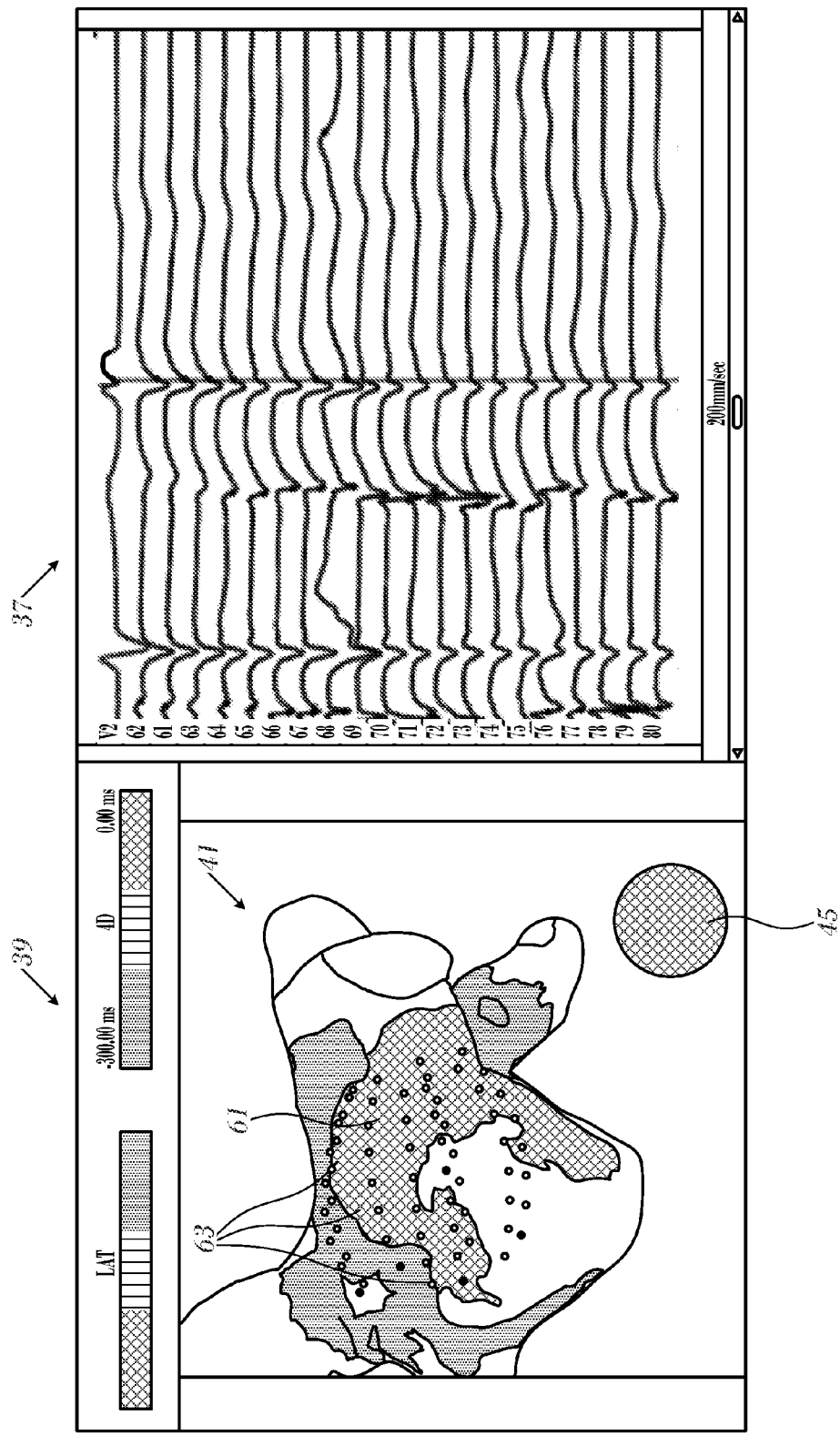
FIG. 5 is a screen display generated by the system shown in FIG. 1 in accordance with an embodiment of the invention.

Reference is now made to FIG. 5, which is a screen display similar to FIG. 2, in accordance with an embodiment of the invention. A large region 61 shows apparent activation, but is coincident with ventricular depolarization, as shown by the illuminated state of the icon 45. The map 41 indicates locations 63 of mapping electrodes of the cardiac catheter (not shown).

While snapshots are necessarily shown in the above-described figures, in practice the operator views a 4-dimensional LAT map, and becomes immediately aware of ventricular depolarization when activation of the icon 45 occurs. This avoids the inconvenience of reference to and interpretation of the extensive data shown on the right pane 37. In particular, the information provided by the icon 45 relates presumptive atrial annotations to ventricular depolarization. When a presumptive annotation is represented at an atrial location on the map 41 the operator can immediately determine if ventricular depolarization is present at the same time. If so, the event is suspect as being a false annotation because it may be corrupted by far-field signals from the ventricle.

Operation

Figure 6:
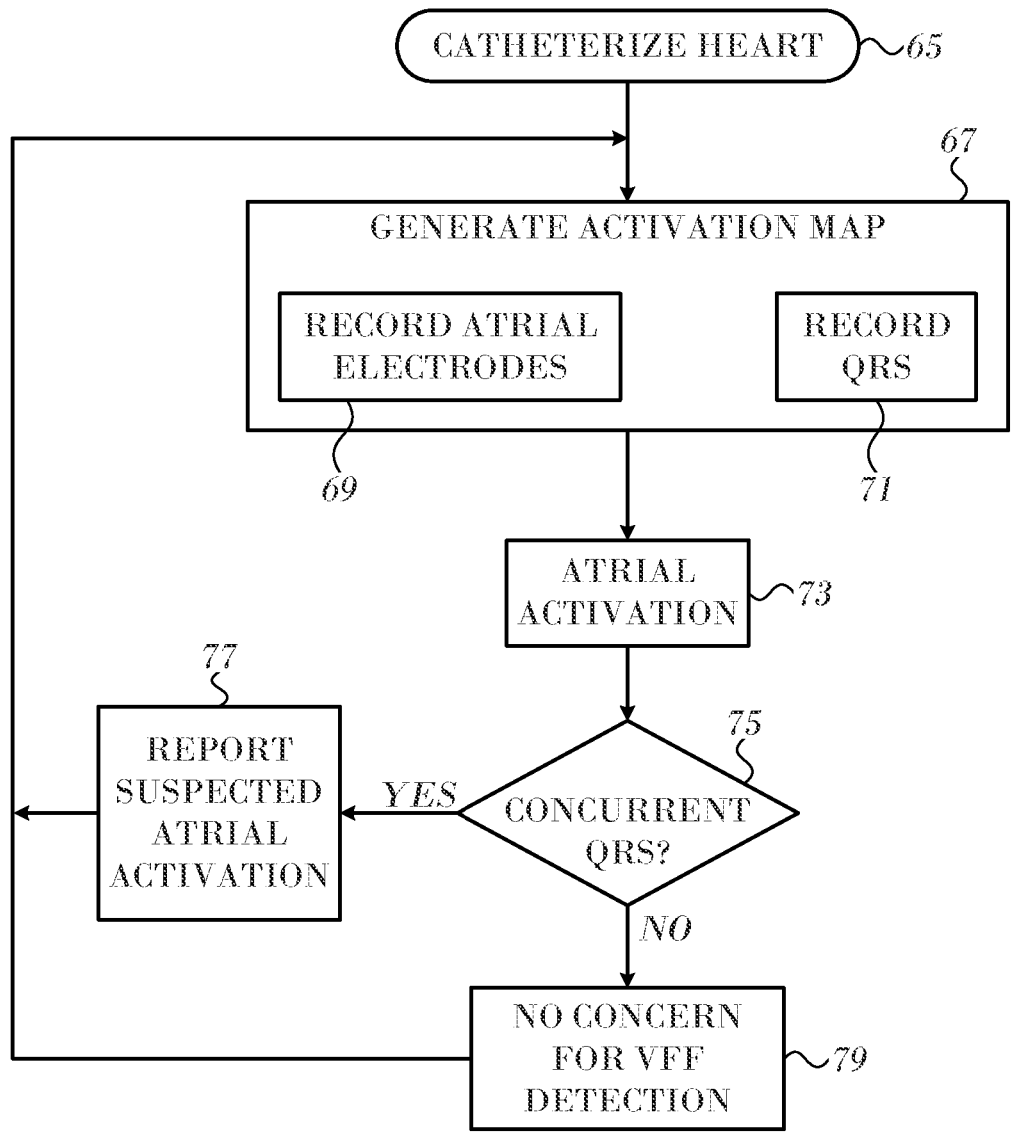
FIG. 6 is a flow-chart of a method of indicating ventricular electrical activity during atrial mapping in accordance with an embodiment of the invention.

Reference is now made to FIG. 6, which is a flow-chart of a method of indicating ventricular electrical activity during atrial mapping in accordance with an embodiment of the invention. The process steps are shown in a particular linear sequence in FIG. 6 for clarity of presentation. However, it will be evident that many of them can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the method.

At initial step 65 the heart is catheterized conventionally using any suitable multi-electrode catheter. Catheters such as the PentaRay® NAV or Navistar® Thermocool® catheters, available from Biosense Webster, are suitable for initial step 65. The electrodes of the catheter is placed in galvanic contact with respective locations in one of the atria.

Next, at step 67 recording of cardiac electrical activity occurs and an activation map of the heart is generated. Step 67 comprises step 69 where atrial activity is recorded. Step 69 is usually performed concurrently with the multiple electrodes of the catheter, each having a respective location in the atrium, as indicated in FIG. 5. At the same time ventricular activity is recorded in step 71, for example by using body surface electrodes. QRS complexes or R waves indicative of ventricular depolarization are input to the processor 22 (FIG. 1), which activates of an icon on a graphical user interface, e.g., the icon 45 shown in the preceding figures. The time relationships of ventricular depolarization shown on the graphical display as the same visual scheme as that of the atrial electrodes, except that the visual scheme is linked to ventricular depolarization rather than to depolarization of the atria.

At step 73 atrial depolarization is detected in one or more of the locations of the catheter electrodes.

Control now proceeds to decision step 75, where it is determined if concurrent ventricular depolarization was present concurrently with the atrial depolarization by reference to the above-mentioned icon. If the determination at decision step 75 is affirmative, then control proceeds to step 77. The state of the icon constitutes the operator that the detection of atrial depolarization may not be reliable. The icon thus alerts the operator to the possibility that the detection of atrial depolarization may be a false is a suspect atrial activation, i.e., a false annotation event, and that far-field ventricular activity may be responsible.

If the determination at decision step 75 is negative, then control proceeds to step 79. The detection of atrial depolarization is considered to be valid, and a local activation time of the location in which the atrial depolarization was detected is noted. There is no concern for VFF detection.

After performing step 77 or step 79 control returns to step 67 to iterate the procedure.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method of guiding a catheter medical procedure, comprising:
   providing a catheter, a plurality of body surface electrodes, and a display, wherein the catheter comprises a plurality of sensing electrodes, the sensing electrodes each being adapted to measure electrical activity;
   inserting the catheter into an atrium of a heart of a subject, and positioning said plurality of sensing electrodes at a plurality of respective positions in the atrium;
   detecting electrical activity in the atrium using the sensing electrodes over a time period, said detecting electrical activity comprising detecting local activation times (LAT) at a plurality of locations in the atrium;
   displaying a 4-dimensional LAT map on the display using electrical activity detected by said sensing electrodes in the atrium, the 4-dimensional LAT map comprising a 3-dimensional electroanatomic map which changes over the time period, the 4-dimensional LAT map being color-coded based on a color scale with different colors on the 4-dimensional LAT map indicating electrical activation at different respective times, and same colors on the 4-dimensional LAT map indicating concurrent electrical activation;
   attaching the plurality of body surface electrodes to the patient;
   detecting ventricular activity in the heart of the patient using the body surface electrodes during said time period, said ventricular activity comprising ventricular depolarization, the ventricular depolarization being identified by detecting at least one of a QRS complex and an R wave;
   displaying an icon on the display simultaneous to said displaying of the 4-dimensional LAT map, with the icon changing over the time period, with the icon displayed in an icon color according to said color scale during at least part of the time period, wherein the icon color when present is displayed in response to ventricular depolarization and corresponds to a ventricular depolarization time according to said color scale; and
   detecting both (i) ventricular depolarization and (ii) first electrical activity in the atrium at a first time point which is during said time period, and in response to said detecting of (i) ventricular depolarization and (ii) first electrical activity at the first time point simultaneously displaying both the icon and at least part of the 4-dimensional LAT map in a first color according to the color scale;
   wherein said simultaneous displaying of both the icon and at least part of the 4-dimensional LAT map in the first color indicates that said first electrical activity detected in the atrium potentially comprises a far-field signal from the ventricle.

2. The method of claim 1, further comprising:
   at a second time point during the time period, detecting a second electrical activity in the atrium, and in response to the second electrical activity displaying at least part of the 4-dimensional LAT map in a second color according to the color scale during the second time point;
   wherein ventricular depolarization is not present and is not detected at the second time point, and the icon is displayed in a color according to the color scale other than in the second color at the second time point;
   wherein displaying the icon and at least part of the 4-dimensional LAT in different colors according to the color scale at the second time point indicates that said second electrical activity in the atrium does not include a far-field signal from the ventricle.

3. The method of claim 1, further comprising:
   at a second time point during the time period, detecting a second electrical activity in the atrium, and in response to the second electrical activity displaying at least part of the 4-dimensional LAT map in a second color according to the color scale during the second time point;
   wherein ventricular depolarization is not present and is not detected at the second time point and in response the icon is displayed as inactive on the display, and wherein displaying the icon as inactive comprises displaying the icon otherwise than in a color according to the color scale, the icon then being in an inactive state;
   wherein displaying at least part of the 4-dimensional LAT map in the second color according to the color scale while the icon is inactive indicates that the second electrical activity in the atrium does not include a far-field signal from the ventricle.

4. The method of claim 1, wherein the icon has only one color at a time and is displayed spaced apart from the 4-dimensional LAT map.

5. The method of claim 1, wherein the icon has only one color at a time and is displayed on top of the 4-dimensional LAT map.

6. The method of claim 1, wherein the catheter further comprises an ablation electrode, and wherein the method comprises ablating cardiac tissue.

7. The method of claim 1, wherein the plurality of body surface electrodes comprise ECG leads linked to an ECG monitor, the method comprising detecting ECG signals from the patient using the ECG leads; and
   wherein said detecting ventricular activity comprises identifying ventricular depolarization based on ECG signals.

8. The method of claim 1, further comprising displaying a plurality of tracings on the display, the tracings representing electrical activity detected at said plurality of positions in the atrium using the sensing electrodes over at least part of the time period; and
wherein the time period comprises at least one cardiac cycle.

9. The method of claim 1, further comprising:
displaying a plurality of tracings on the display, the tracings extending horizontally and representing electrical activity detected at said plurality of positions in the atrium using the plurality of sensing electrodes over time; and
displaying a vertical line on the tracings, the vertical line crossing the tracings at points corresponding to electrical data which is currently being displayed on the 4-dimensional LAT.

10. The method of claim 1, further comprising:
detecting both (i) ventricular polarization and (ii) first electrical activity in the atrium at a first time point which is during said time period, and in response to said detecting of (i) ventricular polarization and (ii) first electrical activity at the first time point simultaneously displaying both the icon and a first part of the 4-dimensional LAT map in a first color according to the color scale, and simultaneously displaying a different second part of the 4-dimensional LAT map in a second color according to the color scale;
wherein said simultaneous displaying of both the icon and the first part of the 4-dimensional LAT map indicates that first electrical activity detected in a first area of the atrium corresponding to the first part of the 4-dimensional LAT map potentially comprises a far-field signal from the ventricle; and
wherein said simultaneous display of the second part of the 4-dimensional LAT map in the second color indicates that second electrical activity detected in a corresponding second area of the atrium does not include a far-field signal from the ventricle.

11. The method of claim 1, further comprising:
during said first time point, displaying part of the 4-dimensional LAT map in a second color according to the color scale, thereby indicating that a portion of the electroanatomical map displayed in the second color does not include a far-field signal from the ventricle.

12. A cardiac monitoring device comprising:
a console comprising a processor, and a computer-readable memory linked to the processor and holding programs and data objects;
wherein the console is operatively connectable to a display, an electrocardiographic sensor, and a catheter comprising a plurality of sensing electrodes;
wherein when the console is operatively connected to said display, electrocardiographic sensor, and catheter, execution of the programs by the processor causes the cardiac monitoring device to perform the steps of:
receiving electrical activity from said plurality of sensing electrodes when said catheter is positioned in an atrium of a heart of a patient and operatively connected to the console, the electrical activity comprising local activation times (LAT) for a plurality of locations in the atrium;
displaying on the display a 4-dimensional LAT map representing electrical activity detected by sensing electrodes in the atrium, the 4-dimensional LAT map comprising a 3-dimensional electroanatomic map which changes over a time period, the 4-dimensional LAT map being color-coded based on a color scale with different colors on the 4-dimensional LAT map indicating electrical activation at different respective times, and same colors on the 4-dimensional LAT map indicating concurrent electrical activation;
when the electrographic sensor is applied to the patient, receiving ventricular activity data from the electrographic sensor during the time period, said ventricular activity data comprising at least one of a QRS complex and an R wave indicative of ventricular depolarization;
using the display, displaying on the display an icon simultaneous to said displaying of the 4-dimensional LAT map, with the icon changing over the time period, with the icon displayed in an icon color according to said color scale during at least part of the time period, wherein the icon color when present is displayed in response to ventricular depolarization detected using the electrographic sensor, and corresponds to a ventricular depolarization time according to said color scale; and
detecting both (i) ventricular depolarization and (ii) first electrical activity in the atrium at a first time point which is during said time period, and in response to said detecting of (i) ventricular depolarization and (ii) first electrical activity at the first time point simultaneously displaying both the icon and part of the 4-dimensional LAT map in a first color according to the color scale;
wherein said simultaneous displaying of both the icon and at least part of the 4-dimensional LAT map in the first color indicates that said first electrical activity detected in the atrium potentially comprises a far-field signal from the ventricle.

13. The cardiac monitoring device according to claim 12, the device further comprising a display, an electrocardiographic sensor, and a catheter comprising a plurality of sensing electrodes;
wherein the display, the electrocardiographic sensor, and the catheter are operatively connected to the console.

14. The cardiac monitoring device according to claim 12, the device further comprising a display, an electrocardiographic sensor comprising a plurality of body surface electrodes, and a catheter comprising a plurality of sensing electrodes.

15. The cardiac monitoring device according to claim 12, wherein execution of the programs by the processor causes the cardiac monitoring device to perform the additional steps of:
at a second time point during the time period, receiving a second electrical activity comprising local activation times (LAT) for a plurality of locations in the atrium from the plurality of sensing electrodes;
in response to the second electrical activity, displaying on the display at least part of the 4-dimensional LAT map in a second color according to the color scale during the second time point;
wherein ventricular depolarization is not present and is not detected at the second time point, and in response to not detecting ventricular depolarization at the second time point, the icon is one of: (a) displayed in a third color according to the color scale, or (b) displayed in an inactive state which comprises displaying the icon otherwise than in a color according to the color scale, during the second time point;

wherein said displaying of the icon during the second time point indicates that the second electrical activity in the atrium does not include a far-field signal from the ventricle.

16. The cardiac monitoring device according to claim 12:
the cardiac monitoring device according to claim 12, the device further comprising a display, an electrocardiographic sensor, and a catheter comprising a plurality of sensing electrodes;
wherein the display, the electrocardiographic sensor, and the catheter are operatively connected to the console;
wherein execution of the programs by the processor causes the cardiac monitoring device to perform the additional steps of:
during said first time point, displaying part of the 4-dimensional LAT map in a second color according to the color scale, thereby indicating that a portion of the electroanatomical map displayed in the second color does not include a far-field signal from the ventricle.

17. A method of guiding a catheter medical procedure, comprising:
providing a console comprising a processor, a catheter, an electrocardiographic sensor, and a display, wherein the catheter comprises a plurality of sensing electrodes, the sensing electrodes each being adapted to measure electrical activity;
inserting the catheter into an atrium of a heart of a subject, and positioning said plurality of sensing electrodes at a plurality of respective positions in the atrium;
detecting electrical activity in the atrium using the sensing electrodes over a time period, said detecting electrical activity comprising detecting local activation times (LAT) at a plurality of locations in the atrium;
displaying an electroanatomical map on the display using electrical activity detected by said sensing electrodes in the atrium, the electroanatomical map being color-coded based on a color scale with different colors indicating electrical activation at different respective times, and same colors on the electroanatomical map indicating concurrent electrical activation;
applying the electrocardiographic sensor to the patient;
detecting ventricular activity in the heart of the patient using the electrocardiographic sensor during said time period, said ventricular activity comprising ventricular depolarization,
displaying an icon on the display simultaneous to said displaying of the electroanatomical map, with the icon changing over the time period, with the icon displayed in an icon color according to said color scale during at least part of the time period, wherein the icon color when present is displayed in response to the electrocardiographic sensor detecting ventricular depolarization and corresponds to a ventricular depolarization time according to said color scale; and
detecting both (i) ventricular depolarization and (ii) first electrical activity in the atrium at a first time point which is during said time period, and in response to said detecting of (i) ventricular depolarization and (ii) first electrical activity at the first time point simultaneously displaying both the icon and at least part of the electroanatomical map in a first color according to the color scale during the first time point;
wherein said simultaneous displaying of both the icon and at least part of the electroanatomical map in the first color indicates that said first electrical activity detected in the atrium potentially comprises a far-field signal from the ventricle.

18. The method according to claim 17:
wherein the electrocardiographic sensor comprises a plurality of body surface electrodes positioned on the patient;
the method comprising detecting ventricular activity using the body surface electrodes; and
wherein the step of detecting ventricular depolarization comprises identifying at least one of a QRS complex and an R wave in the patient.

19. The method according to claim 17, further comprising:
at a second time point during the time period, detecting a second electrical activity using the sensing electrodes in the atrium, the second electrical activity comprising local activation times (LAT) at a plurality of locations in the atrium;
in response to the second electrical activity, displaying on the display at least part of the electroanatomical map in a second color according to the color scale during the second time point;
wherein ventricular depolarization is not present and is not detected at the second time point, and in response to not detecting ventricular depolarization at the second time point, the icon is one of: (a) displayed in a color according to the color scale other than the second color, or (b) displayed in an inactive state which comprises displaying the icon otherwise than in a color according to the color scale, during the second time point;
wherein said displaying of the icon during the second time point indicates that the second electrical activity in the atrium does not include a far-field signal from the ventricle.

20. The method according to claim 17, further comprising:
during said first time point, displaying part of the electroanatomical map in a second color according to the color scale, thereby indicating that a portion of the electroanatomical map displayed in the second color does not include a far-field signal from the ventricle; and
wherein the icon includes at most a single color according to the color scale at any given time point.

* * * * *